United States Patent [19]

Beyschlag

[11] Patent Number: 5,562,599
[45] Date of Patent: Oct. 8, 1996

[54] URETHRAL DAMMING DEVICE

[76] Inventor: Heinz G. Beyschlag, Eichbergweg 11, 73529 Schwäbish Gmünd, Germany

[21] Appl. No.: 370,423

[22] Filed: Jan. 9, 1995

[30] Foreign Application Priority Data

Feb. 8, 1994 [DE] Germany ............... 9402017 U

[51] Int. Cl.$^6$ ................................................. A61F 2/02
[52] U.S. Cl. ................................................. 600/29
[58] Field of Search ............... 128/DIG. 25, 842–844; 600/29–32; 602/77; 604/904

[56] References Cited

U.S. PATENT DOCUMENTS

| | | | |
|---|---|---|---|
| 2,649,854 | 8/1953 | Salm | 600/29 |
| 4,968,294 | 11/1990 | Salama | 600/30 |
| 4,981,465 | 1/1991 | Ballan et al. | 128/DIG. 25 X |

FOREIGN PATENT DOCUMENTS

| | | |
|---|---|---|
| 0188376 | 7/1986 | European Pat. Off. . |
| 0218203 | 4/1987 | European Pat. Off. . |
| 2600259 | 8/1976 | Germany ............... 128/DIG. 25 |
| 2904169.8 | 8/1980 | Germany . |
| 3430873.3 | 1/1986 | Germany . |
| 3633824.9 | 4/1988 | Germany . |

*Primary Examiner*—Angela D. Sykes
*Assistant Examiner*—Samuel Gilbert
*Attorney, Agent, or Firm*—Nixon & Vanderhye P.C.

[57] ABSTRACT

Urethral damming device for preventing uncontrolled discharge of urinary fluid in incontinent patients includes an elongate body formed of a flexible, resilient biocompatible material adapted to being inserted within a patient's urethra. The elongate body has a closed anterior end, an open posterior end, and an annular wall joining the anterior and posterior ends. The annular wall defines an interior recessed cavity which extends axially from the open posterior end of the elongate body toward the anterior end thereof. In use, the cavity receives urinary fluid passing through the patient's urethra which causes a pressure to be exerted upon the interior surface of the annular wall. This outward pressure responsively causes the annular wall to be flexed outwardly into sealing relationship with the patient's urethra. As a result, uncontrolled discharge of the urinary fluid is prevented.

10 Claims, 1 Drawing Sheet

URETHRAL DAMMING DEVICE

CLAIM FOR PRIORITY UNDER 35 USC §119

This application is based on, and claims priority under 35 USC §119 from, German Utility Model Application No. G94 02 017.5 filed in Germany on Feb. 8, 1994, the entire content of such priority application being incorporated expressly hereinto by reference.

FIELD OF INVENTION

The present invention relates generally to devices which control patient incontinence. The present invention more specifically relates to devices which are insertable into a patient's urethra so as to provide an effective dam against uncontrolled urinary discharge.

BACKGROUND AND SUMMARY OF THE INVENTION

Persons afflicted with incontinence (i.e., the inability of a person intentionally to retain and void urinary fluid) experience greatly impaired normal life functions and substantial psychological stress. Substantial effort has therefore been made to fashion technical devices to assist persons afflicted with incontinence, such a absorbing devices (e.g., absorbent pads worn externally over the patient's urethra orifice), external collection systems and internally placed urinary fluid drainage systems.

A closure or damming device for male urethras has been proposed in DE-OS 19 57 693 which is formed from a short, slender, elastic tube of soft rubber closed at its posterior end and open and its anterior end. The interior of the tube is provided with a holding device that is placed into the tube's open anterior end and is connected securely to the tube. The holding device is operated by means of a head part which projects beyond the anterior end of the tube. That is, by turning a screw placed in the head part, and with the help of a number of spreader levers, the tube is stretched far enough so the closure device is held firmly in the urethra sufficiently to effect urethral closure.

The device disclosed in DE-OS 19 57 693 has several disadvantages. For example, it is not leak-proof. When the tube is stretched, the spreader levers form a polygon such that two parallel surfaces that cannot be leak-proof are formed between the bearing points. To make such surfaces leak-proof, therefore, the elastic forces would have to be infinitely great. Furthermore, the head part disadvantageously projects beyond the external orifice of the urethra and consequently is disruptive to wear—that is, on the one hand, the weight of the head part affects and hurts the urethra and its surrounding tissue, while on the other hand, pain is caused by friction (e.g., with the penis and glans).

What has been needed in this art therefore, is a device for controlling incontinence which is "user-friendly". That is, what has been needed is an economical and environmentally safe incontinence control device which allows the user to insert/remove the device without external medical assistance; is lightweight so as to promote optimal comfort when inserted; and ensures that a secure and absolutely leak-proof damming effect of the urethra is achieved. It is towards fulfilling such needs that the present invention is directed.

Broadly, the present invention is embodied in a urethral damming device which has a closed anterior end and an open posterior end. The device most preferably includes a unitary body formed of a flexible, resilient biocompatible material which has an interiorly recessed hollow cavity extending from the open posterior end lengthwise towards the closed anterior end. The device of this invention therefore does not have any separately installed components which could affect its weight and wearing comfort.

The recessed hollow cavity most preferably defines the generatrices of an elliptical parabolic surface, but could perform equivalent functions if it was formed into a generally cylindrical or conical shape. The device is sufficiently elongate to allow its external surface to press sealingly against the urethral tissue, but not extending longer than the urethral tract. As a result, the device of this invention can satisfactorily be used in the male urethral anatomy.

In preferred forms, the device of this invention will have a flexible recovery element (e.g., a length of thread) attached to the closed anterior end of the device and adapted to extend externally of the urethra orifice. As a result, the user may simply pull on the flexible recovery element so as to remove the device from its position within that person's urethra.

The device of this invention is preferably configured so as to have an approximate geometric shape corresponding to an elliptical paraboloid. However, the device can also be configured in other geometric shapes, such as approximately cylindrical or conical. The maximum length of the device is the length of the male patient's urethra in which the device will be placed. However, in practice, the length of the device is substantially shorter than the length of the male patient's urethra, for example, between about 2 to about 5 cm.

The device is placed in the patient's urethra so that its closed anterior end lies flat against, but does not extend beyond, the exterior urethral orifice (e.g., posteriorly of the meatus urinarius). The device is preferably formed as a unitary body of a flexible, resilient, biocompatible material (e.g., silicone rubber). The hollow interior recessed cavity most preferably has a wall thickness which is greater in the region of the closed anterior end and gradually tapers toward the open posterior end. With such an arrangement, it has been found that the device of the present invention may be securely seated within the patient's urethra so that it lies against the urethral walls to form a leak-proof seal therewith.

Presumably, the leak-proof seal established by the device of this invention can be attributed to the pressure in the bladder which is transferred by the urinary fluid column within the urethra to the interior of the device. This transferred pressure is therefore believed to elastically expand the flexible wall which annularly surrounds and defines the recessed hollow cavity in the device of this invention thereby causing the walls to press sealingly against the urethral tissue. The contact pressure therefore presumably changes in proportion of the pressure transferred by the urinary fluid column within the urethra. As a result, increasing pressure exerted by the urinary fluid within the recessed hollow cavity will translate into increased contact pressure between the urethra tissue and the external surfaces of the device. Since the device is formed from a flexible material, the exterior surfaces of the device will conform to irregularities of the urethra tissue. The device of this invention may also be prestressed so that the wall which annularly surrounds the interior recessed cavity is inherently biased to expand within the urethra and thereby ensure a leak-proof seal even in the absence of a urinary fluid column.

Further aspects and advantages of this invention will become more clear after careful consideration is given to the following detailed description of the preferred exemplary embodiment.

BRIEF DESCRIPTION OF THE DRAWINGS

Reference will hereinafter be made to the accompanying drawings wherein like reference numerals throughout the various FIGURES denote like structural elements, and wherein.

DETAILED DESCRIPTION OF THE PREFERRED EXEMPLARY EMBODIMENTS

Figure 1:
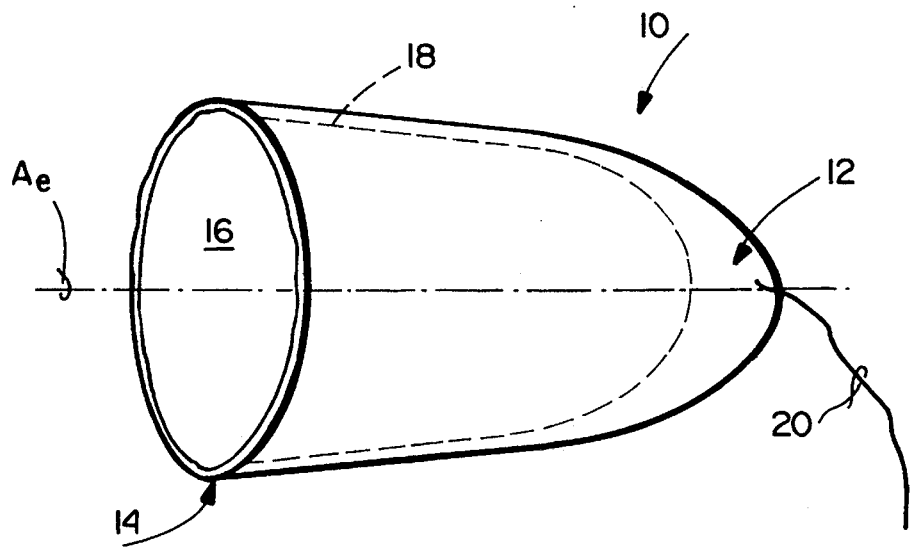
FIG. 1 is a perspective view of a urethral damming device which embodies the present invention.

Accompanying FIG. 1 depicts a preferred urethral damming device 10 in accordance with the present invention in a greatly enlarged manner for clarity of presentation and discussion. As can be seen, the device 10 is comprised of a unitary elongate body formed of a flexible, resilient, biocompatible material. Most preferably, the device is in the form of an elongate elliptical paraboloid, but other geometric configurations (e.g., cylindrical, conical or the like) may be provided.

Important to the present invention, the device 10 is closed at its anterior end 12 and open at its posterior end 14. A central recessed interior cavity 16 extends axially from the open posterior end 14 towards the closed anterior end 12.

The annular wall 18 which surround and defines the interior cavity 16 most preferably has a thickness dimension which is greater near the anterior end 12 and tapers gradually toward the open posterior end 14. The thicker dimension of the wall 18 near the anterior end 12 as compared to the thickness dimension of the wall 18 near the poster end 14 is important to make the device 10 less susceptible to radial compression near the anterior end and to permit safe removal of the device 10. The thinner wall 18 near the posterior end 14 thereby promotes greater elasticity and flexibility of the material so as to promote good fit and secure sealing with the tissue of the mucous membrane of urethra wall $U_w$. The anterior end 12 is thus formed of a solid mass of the material from which the device 10 is made. In order to assist in removal of the device 10, a flexible recovery element 20 (such as a thread) may be attached to the anterior end 12 (e.g., by embedding the element in the mass of material forming the anterior end 12).

Figure 2:
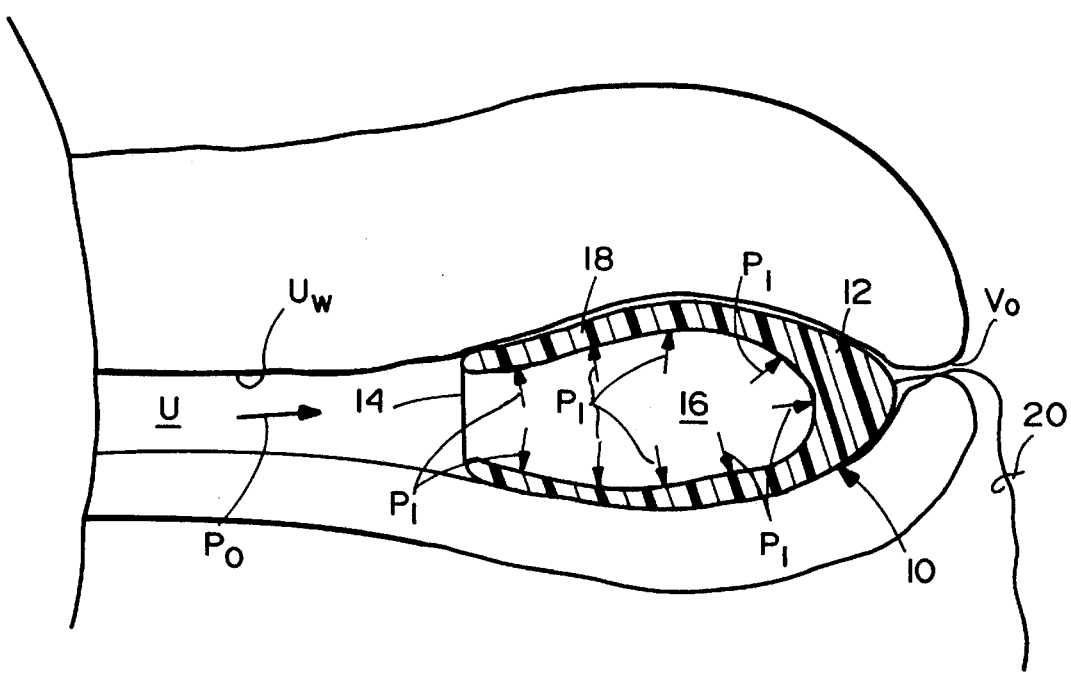
FIG. 2 is a cross-sectional schematic view of the urethral damming device shown in FIG. 1 positioned within the urethra of a male.

In use, the device 10 is placed within a patient's urethra U so that it is positioned immediately posteriorly of the meatus urinarius as shown in FIG. 2. The flexible recovery element 20 will, however, extend through exterior urethra orifice $U_o$ so as to be accessible to assist the patient in removing the device 10. In order to insert the device 10 within the urethra U, the device is compressed radially (i.e., relative to the elongate axis $A_e$ shown in FIG. 1) at the open proximal end 14. The posterior end 14 of the device 10 will thus assume a slender, tube-like object which may be inserted initially into the urethra U through the exterior urethra orifice $U_o$. The anterior end 12 may then be pushed in a posterior direction until it lies entirely within the urethra U, for example, so that it is positioned immediately posteriorly of the meatus urinarius. The device 10 may thus radially expand once positioned in the urethra U so that it lies in sealing contact with the surrounding tissue of the urethral wall $U_w$. Only the recovery element 20 projects through the exterior urethra orifice so that it may be grasped and pulled so as to assists in removal and recovery of the device 10 from within the urethra U.

The wall 18 which annularly surrounds the recessed interior cavity 16 is most preferably prestressed so that it inherently radially expands into sealing contact with the tissue of the urethral wall $U_w$. An overall pressure (symbolized by the arrow $P_0$ in FIG. 2) created by the sum of the pressures of the bladder and the urinary fluid column within the urethra U will thus be distributed in the cavity 16 and exerts an outward pressing force against the interior of the wall 18 (symbolized by arrows $P_1$ in FIG. 2). When the bladder is empty and there is no urinary fluid column, the prestressing of wall 18 is sufficient to maintain the device 10 in leak-proof contact with the tissue of the urethra wall $U_w$. With increasing formation of a urinary fluid column within the urethra U, however, an overall pressure (arrow $P_0$) is formed that is distributed evenly along the interior of wall 18 sufficient to further sealingly press (arrows $P_1$) the exterior surface of the wall 18 against the tissue of the urethral wall $U_w$. These pressing forces (arrows $P_1$) are proportional to the overall pressure (arrow $P_0$) — that is, the greater the overall pressure, the greater the pressing forces. Consequently, the wall 18 will be more firmly pressed against the tissue of the urethral wall $U_w$ with an increase in the pressure created by a urinary fluid column within the urethra U. The overall pressure (arrow $P_0$) within the urethra U which acts perpendicularly to the anterior end 12 is not, however, sufficiently great to deform the solid mass of material forming the anterior end 12 to an extent that it would be forced through the exterior urethra orifice $U_o$.

The recovery element 20 is used to remove the device 10 from the urethra U. That is, upon a pulling force being manually exerted on the recovery element 20, the device 10 can be pulled from the urethra U through the exterior urethra orifice $U_o$. The pulling forced exerted on the recovery element 20 causes the device 10 to be stretched along its elongate axis $A_e$ to an extent that it becomes longer and narrower so as to make its profile sufficiently small to allow easy passage through the exterior urethra orifice $U_o$. At the same time, the lengthening and narrowing of the device 10 will loosen the fluid-tight seal between the wall 18 and the tissue of the urethral wall 18 thereby allowing the device to be removed without great resistance and thus without the patient experiencing great pain.

The urethra damming device 10 of this invention has a relatively simple design, is easy to produce and completely achieves its intended purpose. The use of the device 10 in accordance with this invention achieves several distinct advantages as compared to known prior art devices. For example, the danger of infection that causes various problems with known devices placed internally in the body, especially with catheters, is practically no longer possible when the device 10 of this invention is used correctly. The device 10 is inserted into the urethra in a sterile state and must be removed (i.e., pulled out from the urethra) every time the patient's bladder is voided. If it is assumed that an average of about four to six bladder voidings occur per day, then the device of this invention is at most positioned within the patient's urethra for five hours. The relatively short periods of use also prevent the device from being susceptible to fluid leakage since a fresh device is employed each time a patient's bladder is voided. Germs or other infective agents possibly nested in the urethra are furthermore cleansed every time the bladder is voided. The feared "supergrowth" of germs in the bladder and/or in other organs in this area is therefore not to be expected with proper use of the device according to the present invention. Furthermore, bladder disorders caused by "supergrowing" agents in conventional catheter drainage systems are precluded since no leg pouch or catheter are used.

One important practical advantage in using the urethra damming device in accordance with the present invention is that the incontinent patient is truly "mobile". That is, an incontinent patient may freely move about for extended time periods without impairment from conventional incontinent products such as diaper inserts, catheter/leg pouch drainage systems, and the like. Unpleasant noise when a person's bladder is voided that is associated with some incontinent products (e.g., diaper pants) no longer occur with the use of the present invention. Furthermore, the patient's genital area remains dry thereby preventing skin irritation with its attendant soreness. The patient can again socially interact with other people without psychological stress from their incontinence disorder.

Many bedridden patients are also allowed to be "mobile" since they are no longer tied constantly to a bed by a catheter drain. Sever bedridden patients (especially physically weaker older persons) thereby are not exposed to other maladies, such as pneumonia, which can sometimes occur with prolonged immobility. Furthermore, the ability of the present invention to allow mobility of bedridden incontinent patients not only renders unnecessary any external bladder drainage apparatus that may be associated with that patient, but can also reduce the risks of appetite loss, cardiovascular disorder and bedsores. Significant cost savings for that patient's health care could thereby be realized by use of the present invention. The mobile patient also does not need to be transported to hospitals and/or doctors by professional ambulances resulting in even further cost savings.

The device of this invention is, moreover, environmentally friendly since it is formed from a small amount of biocompatible material which can be cleaned and recycled to form new devices. While sterile packaging is needed, the amount of such packaging will be quite small due to the small size of the device. Unlike conventional incontinent products such as diapers or absorbent pads, there is no substantial disposal problem associated with the use of the device according to the present invention.

Finally, the device of this invention is economical to produce since it is formed as a one-piece structure which lends itself to mass production. As a result, large quantities of the device may be formed in various sizes to fit particular patients' needs in a cost-effective manner.

Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A urethral damming device for preventing uncontrolled discharge of urinary fluid in incontinent patients, said device comprising an elongate body formed of a flexible, resilient biocompatible material adapted to being inserted within a patient's urethra, said elongate body having a closed anterior end, an open posterior end, and an annular wall joining said anterior and posterior ends, said annular wall defining an interior recessed cavity which extends axially from said open posterior end of the body toward said anterior end thereof, wherein said cavity receives urinary fluid passing through the patient's urethra which causes an outward pressure to be exerted upon an interior surface of said annular wall, and wherein said outward pressure responsively causes said annular wall to be flexed outwardly into sealing relationship with the patient's urethra, whereby uncontrolled discharge of said urinary fluid is prevented.

2. The device of claim 1, wherein said annular wall is prestressed such that said annular wall is adapted to expand outwardly into sealing contact with the patient's urethra in the absence of said cavity receiving urinary fluid therein.

3. The device of claim 1, wherein said biocompatible material is a silicone rubber.

4. The device of claim 1, wherein said elongate body has a length of between about 2 to about 5 centimeters.

5. The device of claim 1, further comprising a flexible recovery element attached to said anterior end of said elongate body.

6. The device of claim 5, wherein said recovery element is a thread.

7. The device of claim 1, wherein said annular wall has a thickness dimension which is greater near said anterior end as compared to its thickness dimension near said posterior end.

8. The device of claim 7, wherein the thickness dimension of said annular wall gradually tapers from said anterior end to said posterior end.

9. The device of claim 1, wherein the elongate body has a shape approximating an elliptical paraboloid.

10. The device of claim 1, wherein the elongate body has an approximately cylindrical or conical shape.

* * * * *